United States Patent [19]

Beavers

[11] Patent Number: 4,740,639

[45] Date of Patent: Apr. 26, 1988

[54] PROCESS FOR PREPARATION OF 2,4-DISUBSTITUTED-1,5-PENTANEDIOLS

[75] Inventor: William A. Beavers, Longview, Tex.

[73] Assignee: Eastman Kodak Company, Rochester, N.Y.

[21] Appl. No.: 60,791

[22] Filed: Jun. 12, 1987

[51] Int. Cl.$^4$ .................... C07C 29/14; C07C 31/20; C07C 45/45; C07C 47/12

[52] U.S. Cl. .................... 568/853; 568/433; 568/464; 568/809; 568/461

[58] Field of Search .................... 568/464, 853, 809

[56] References Cited

U.S. PATENT DOCUMENTS

| | | | |
|---|---|---|---|
| 2,639,295 | 5/1953 | Hagemeyer | 568/464 |
| 4,122,290 | 10/1978 | Immel et al. | 568/464 |
| 4,181,810 | 1/1980 | Immel et al. | 568/464 |
| 4,346,239 | 8/1982 | Bach et al. | 568/464 |

FOREIGN PATENT DOCUMENTS 2037769  7/1980  United Kingdom ............... 568/464

*Primary Examiner*—J. E. Evans
*Attorney, Agent, or Firm*—Thomas R. Savitsky; John F. Stevens; William P. Heath, Jr.

[57] ABSTRACT

The invention relates to a process for the preparation of 2,4-disubstituted-1,5-pentanediols from formaldehyde and at least one simple aldehyde of the formula RCH$_2$CHO. More particularly the invention relates to a reaction to produce a 2,4-disubstituted glutaraldehyde wherein the reactant mole ratio of aldehyde/formaldehyde is between 1 and 8. The reaction is carried out in the presence of a secondary amine or secondary amine salt catalyst and leads to higher yields of the 2,4-disubstituted glutaraldehyde. The invention also relates to the production of 2,4-disubstituted-1,5-pentanediols by hydrogenation of the 2,4-disubstituted glutaraldehydes.

8 Claims, No Drawings

PROCESS FOR PREPARATION OF 2,4-DISUBSTITUTED-1,5-PENTANEDIOLS

FIELD OF THE INVENTION

This invention relates to a method of preparing 2,4-disubstituted-1,5-pentanediols. The invention also relates to a method of preparing 2,4-disubstituted glutaraldehydes which are formed as an intermediate in the preparation of the 2,4-disubstituted-1,5-pentanediols.

BACKGROUND OF THE INVENTION 2,4-disubstituted-1,5-pentanediols have been explored for use as flexibilizing glycols in polyester and polyurethane applications. Their preparation has been disclosed previously in U.S. Pat. No. 3,046,311 (Milligan). Milligan initially prepared 2,4-disubstituted-crotonaldehydes by self-aldol condensation of simple aldehydes. For example, self-aldol condensation of n-butyraldehyde gives 2-ethyl-2-hexenal (2,4-diethylcrotonaldehyde) which is used primarily as the precursor to the plasticizer alcohol, 2-ethyl-1-hexanol. These 2,4-disubstituted-crotonaldehydes are in turn condensed with formaldehyde followed by hydrogenation of the resultant 2,4-disubstituted-4-methylol crotonaldehydes to form the 2,4-disubstituted-1,5-pentanediols. However, nuclear magnetic resonance spectroscopy confirms the coproduction of 2,2-disubstituted-1,3-propanediols of the same formulas as structural isomers of the pentanediols. Moreover, these isomers are inseparable by the usual physical methods (fractional crystallization, distillation and chromatography). The quantity of the undesirable propanediols may vary from 5 to .25 percent depending upon the original aldol condensation reaction conditions. This variability in the quantity of the inseparable isomers results in an unacceptable variability in the properties of the finished glycol.

The results of Milligan also indicated a yield of 15 to 63 percent of the 2,4-disubstituted-1,5-pentanediols depending upon the starting crotonaldehyde and even lower yields based on formaldehyde. These low yields are commercially undesirable.

Accordingly, it was undertaken to develop a method of synthesizing 2,4-disubstituted-1,5-pentanediols which produced better yields than the Milligan process and also reduced the amount of undesirable structural isomers coproduced by the reaction. Exploration of different reaction conditions using the catalysts of Milligan showed no improvement in product purities or yield.

Further investigation revealed the possibility of eliminating a reaction step from the Milligan process to thereby improve product purity and yield. Since the reaction of the dialkylcrotonaldehydes with formaldehyde and the reaction of simple aldehydes to form the dialkylcrotonaldehydes are both aldol condensations, the possibility existed to combine these two reaction steps into a single step by condensing two moles of simple aldehyde with one mole of formaldehyde to form the precursor to the 2,4-disubstituted-1,5-pentanediols.

This concept did not initially lead to a useful process since the major product was still the 2,4-disubstituted crotonaldehyde after reaction in the presence of caustic catalyst under the usual aldol condensation conditions. Milder aldol condensation catalysts such as triethylamine showed little improvement. However, the employment of secondary amines and their acid salts led to clearly superior results.

These secondary amine catalysts and their acid salts generally fall into the category of enamine catalysts or Mannich catalysts. Enamine or Mannich catalysts are known to aid the condensation of simple aldehydes with formaldehyde to yield alpha-methylol aldehydes or, upon dehydration, alpha-methylene aldehydes (alpha-alkyl acrolein). Farberov, Mironov, and Korshunov, Chem. Abs., 59, 394 (1963), for example, details the high yield Mannich reaction of butyraldehyde with formaldehyde to form alpha-ethyl acrolein by using stoichiometric quantities of dimethylaminehydrochloride as the Mannich reagent. However, this reaction does not produce the 2,4-disubstituted glutaraldehydes needed as an intermediate for the production of 2,4-disubstituted-1,5-pentanediols.

Accordingly, it is the primary object of the present invention to provide a process for preparing 2,4-disubstituted-1,5-pentanediols of higher purity and increased yields.

It is a further object of the present invention to provide a process for the direct preparation of 2,4-disubstituted glutaraldehydes from formaldehyde and simple aldehyde.

These and other objects of the present invention will be apparent to one of ordinary skill in the art from the summary and detailed description which follow.

SUMMARY OF THE INVENTION

The present invention relates to a process for preparing 2,4-disubstituted glutaraldehydes by reacting formaldehyde with at least one aldehyde having the formula $RCH_2CHO$, wherein R is selected from hydrogen or an unsubstituted or substituted aliphatic, aromatic or aliphatic/aromatic group, at a mole ratio of the aldehyde to the formaldehyde of about 2 to about 7, a temperature of about 40° C. to about 200° C. and in the presence of a catalytic amount of a compound selected from cyclic and acyclic secondary amines or the acid salts thereof.

The present invention also provides a process for preparing 2,4-disubstituted-1,5-pentanediols by reacting formaldehyde with at least one aldehyde having the formula $RCH_2CHO$, wherein R is selected from hydrogen or an unsubstituted or substituted aliphatic, aromatic or aliphatic/aromatic group, at a mole ratio of the aldehyde to the formaldehyde of about 2 to about 7, a temperature of about 40° C. to about 200° C. and in the presence of a catalytic amount of a compound selected from cyclic and acyclic secondary amines or the acid salts thereof to produce a 2,4-disubstituted glutaraldehyde and hydrogenating the 2,4-disubstituted glutaraldehyde to a 2,4-disubstituted-1,5-pentanediol.

DETAILED DESCRIPTION OF THE PREFERRED EMBODIMENTS

The invention comprises a two-step reaction for the production of 2,4-disubstituted-1,5-pentanediols from formaldehyde and at least one simple aldehyde. The overall equation for this reaction is shown as follows:

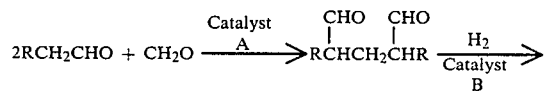

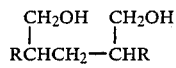

wherein R is hydrogen or an unsubstituted or substituted aliphatic, aromatic or aliphatic/aromatic group.

The first step of the reaction is the production of a 2,4-disubstituted glutaraldehyde from formaldehyde and a simple aldehyde in the presence of a secondary amine or secondary amine salt catalyst. The first step of this reaction is believed to be one of two two-stage reactions. It is believed that there is an initial formation of alpha-substituted acrolein. Unreacted alpha-substituted acrolein may be recovered at the end of the reaction for recycle in subsequent reactions to produce additional 2,4-dialkyl glutaraldehyde and to support the intermediary of this compound in the reaction. This acrolein undergoes either a Michael addition with the simple aldehyde anion formed by the deprotonation of the simple aldehyde by the amine base or a Diels-Alder reaction with the simple aldehyde enamine. In either case the initially formed product is rapidly hydrolyzed to produce the 2,4-disubstituted glutaraldehyde and regenerate the catalyst. In any event it is clear that this reaction step occurs in two stages having different energy requirements.

Formaldehyde is always used as one reactant in the process of the invention. The other reactant must be a simple aldehyde having two hydrogens on the alpha-carbon atom and may be represented by the general formula $RCH_2CHO$ wherein R is hydrogen or a substituted or unsubstituted aliphatic, aromatic or aliphatic/aromatic group. The aliphatic R groups have 1 to 10 carbon atoms and any preferably alkyl groups while the aromatic R groups contain 6 to 18 carbon atoms. The aliphatic/aromatic R groups contain 6 to 28 carbon atoms and include arylakyl and alkaryl groups. Moreover, the substituted R groups may be substituted with nonreactive or slowly reactive functional groups which do not interfere with the reaction of the invention. These functional groups include, but are not limited to, hydroxy, alkoxy, mercapto, thioalkyl, amine, nitrate, nitrite, nitroso, fluoride, alkene and alkyne.

The ratio of simple aldehyde reagent to formaldehyde reagent is important to the outcome of the reaction. In the production of the 2,4-disubstituted glutaraldehyde, stoichiometry demands a ratio of two moles of simple aldehyde reagent to one mole of formaldehyde reagent. However, due to the coproduction of substantial amounts of 2,4-disubstituted crotonaldehydes by the self-aldol condensation of the simple aldehyde, the optimum ratio of the reagents, in practice, is above this level. The reaction will take place over wide ratio ranges but only a portion of these ranges are near optimum. With a very low ratio of simple aldehyde to formaldehyde, formaldehyde is abundant and reacts with reaction products to give copious quantities of polymethylol by-products. With very high ratios, the simple aldehyde is abundant and the reaction produces large quantities of 2,4-disubstituted crotonaldehydes and poly-alkylmethylol by-products from the multiple condensation of simple aldehyde with the aldehyde/formaldehyde condensation product. Accordingly, the preferred simple aldehyde to formaldehyde ratio is between about 2 and about 7 and preferably between about 2.5 and about 3.5.

Suitable catalysts for the first step of this reaction (Catalyst A) include any of a variety of secondary amines or the acid salts of these amines. Included, for example, among this group would be such amines as dimethylamine, diethylamine, dipropylamine, dibutylamine, dibenzylamine, dicyclohexylamine, and diphenylamine; such heterocyclic amines as pyrrolidine, piperidine, and morpholine; such crossed amines as methyl ethyl amine, methyl propyl amine, methyl butyl amine, and ethyl propyl amine; and acid salts of the foregoing amines such as the hydrofluoride, hydrochloride, hydrobromide, hydroiodide, hydrosulfate, hydrophosphate, hydronitrate, and hydroacetate acid salts of the secondary amines.

Useful catalyst A concentrations may vary over a broad range with the understanding that the lower concentrations generally lead to the slower reactions while the higher concentrations permit the reaction to take place under milder conditions. The preferred catalyst A concentration likewise depends on the nature of the catalyst but generally falls in the range of 10M to $10^{-4}$M. A more preferred range is 1M to $10^{-2}$M and the most preferred range is 0.5M to 0.05M. It is to be understood that the reaction still occurs outside of these limits but with unacceptably low rates for the low concentrations or with unacceptably high catalyst usages and by-product formations with the high concentrations.

Likewise the conditions under which the reaction will occur are not critical. It will react preferably from 40° C. to 200° C. or more preferably from 70° C. to 140° C. Since the reaction occurs in two distinct steps with different energy requirements for each step, the most preferable conditions are those which optimize each step. These conditions are 70° C. to 90° C. for the first stage and 100° C. to 140° C. for the second stage.

The residence time for each of these stages depends on the temperature but it translates into the time necessary to permit completion of most of the reactions. The time exposure to the first heating stage is preferably in the 0 to 8 hour range and for the second stage from 1 to 8 hours. A more preferred range is 1 to 6 hours for the first stage and 2 to 6 hours for the second stage. The most preferred range is 2 to 4 hours for each stage with the longer reaction times corresponding to the lower temperatures in each range.

The 2,4-disubstituted glutaraldehyde may be isolated at the end of the first step of the reaction without difficulty. The use of low distillation pressures during isolation will ensure a minimum of decomposition of the 2,4-disubstituted glutaraldehyde during the separation process. It will also permit the isolation of coproducts alpha-alkyl acrolein and 2-formyl-1-alkanol for recycle in subsequent reactions. The 2,4-disubstituted glutaraldehyde may be directly hydrogenated without being isolated or it may be isolated first and then hydrogenated to form 2,4-disubstituted-1,5-pentanediols. The hydrogenation step may be carried out in the presence of any of a variety of hydrogenation catalysts (catalyst B) and under hydrogenation conditions known to those versed in the art of reduction of simple aldehydes. Suitable catalysts for the hydrogenation reaction include, but are not limited to, nickel, palladium, platinum, ruthenium, or rhenium in finely divided state or deposited on such catalyst supports as activated carbon, silica gel, or alumina.

2,4-disubstituted-1,5-pentanediols are useful as components of flexible polyesters or polyurethanes. 1,5-pentanediols are also useful as humectants, coupling agents, insect repellants and in the preparation of esters from monobasic fatty acids such as capric and caprylic acids. Such esters are good plasticizers and synthetic lubricants.

The following examples are presented to further illustrate the process of the invention.

EXAMPLE 1

Butyraldehyde/Formaldehyde Condensation Using Potassium Hydroxide Catalyst

This reaction illustrates the poor yield of glutaraldehydes obtained by the usual aldol condensation routes.

To a 200 mL round bottom flask was charged to 100 mL of 98.5 percent butyraldehyde (1.13 moles), 10 mL of methylalcohol hemiformal (0.17 mole formaldehyde), and the solution was stirred and heated to 40° C. To this solution was added over 45 minutes 25 mL of 4.5M potassium hydroxide (0.113 mole) and the solution was heated and stirred at 40° C. for 2 additional hours and at 90° C. for 1 hour after addition was complete. Gas chromatographic analysis of the product revealed a butyraldehyde conversion of 98.7 percent (formaldehyde conversion of 99.2 percent) with the yield of 2-ethyl-2-hexenal of 63.3 percent (based on butyraldehyde consumed, formaldehyde not being involved in this product) and the yield of the desired product 2,4-diethylglutaraldehyde of 2.1 percent (based on butyraldehyde, 5.7 percent based on formaldehyde).

EXAMPLE 2

Butyraldehyde/Formaldehyde Condensation Using Triethylamine Catalyst

This reaction illustrates the expected product, the acrolein, from this type of aldol condensation reaction.

To a nitrogen flushed 300 mL stainless steel autoclave was charged 120 mL of butyraldehyde (1.36 moles), 30 mL of a methanolic solution of methanol hemiformal (0.51 mole formaldehyde equivalent), and 8.0 mL triethylamine (5.1 volume percent). The run was made with stirring at 80° C. for 4 hours. Analysis of the reaction mixture revealed a butyraldehyde conversion of 63.4 percent and a formaldehyde conversion of 97.5 percent. The yield of 2-ethyl-2-hexenal was 7.5 percent based on butyraldehyde and 2,4-diethyl-1,5-pentanediol precursors was 15.2 percent based on butyraldehyde, 16.4 percent based on formaldehyde. The yield of alpha-ethyl acrolein was 44.1 percent based on butyraldehyde, 47.7 percent based on formaldehyde.

EXAMPLE 3

Butyraldehyde/Formaldehyde Condensation Using Morpholine Catalyst

This reaction illustrates the products generally expected from a Mannich type process. It also illustrates the early stages of the process described in this invention.

Example 2 was repeated substituting 1.23 percent morpholine catalyst for the triethylamine catalyst. Analysis revealed the butyraldehyde conversion to be 59.5 percent and the formaldehyde conversion to be 97.1 percent. The yield of 2-ethyl-2-hexenal was 1.5 percent based on butyraldehyde and the yield of 2,4-diethylglutaraldehyde was 5.1 percent based on butyraldehyde, 5.2 percent based on formaldehyde. The yield of alpha-ethyl acrolein was 28.7 percent based on butyraldehyde, 29.0 percent based on formaldehyde and the yield of 2-formyl-1-butanol was 50.9 percent based on butyraldehyde, 51.6 percent based on formaldehyde.

EXAMPLE 4

Butyraldehyde/Formaldehyde Condensation Using Morpholine Catalyst

This example illustrates the moderate production of 2,4-diethylglutaraldehyde by one of the catalysts of this invention.

Example 3 was repeated except that it was heated first to 80° C. for 4 hours and then at 120° C. for 4 hours. Analysis of the reaction mixture revealed a butyraldehyde (formaldehyde) conversion of 87.6 percent (97.8 percent) and yield based on butyraldehyde (formaldehyde) of 11.7 percent 2-ethyl-2-hexenal, 47.9 percent (50.8 percent) 2,4-diethylglutaraldehyde, 22.7 percent (24.1 percent) alpha-ethylacrolein, and 2.3 percent (2.4 percent) 2-formyl-1-butanol.

EXAMPLE 5

Butyraldehyde/Alpha-Ethylacrolein Conversion Using Morpholine Catalyst

This example shows that the coproducts alpha-ethylacrolein and 2-formyl-1-butanol, which form alpha-ethylacrolein by dehydration during distillation, may be recycled in the process to yield additional 2,4-diethylglutaraldehyde.

Example 4 was repeated except that the autoclave was charged with 70 ml butyraldehyde (0.79 mole), 80 ml of freshly distilled alpha-ethylacrolein (0.76 mole), and 1.25 wt percent morpholine catalyst. Analysis of the reaction mixture revealed a butyraldehyde conversion of 56.1 percent and an alpha-ethylacrolein conversion of 47.6 percent. Based on butyraldehyde (alpha-ethylacrolein) consumed, the yield of 2,4-diethylglutaraldehyde was 68.7 (84.2) percent and of 2-ethyl-2-hexenal was 18.9 percent.

EXAMPLE 6

Propionaldehyde/Formaldehyde Condensation Using Morpholine Catalyst

This example reveals the variability in the yield of the desirable glutaraldehyde on using different starting aldehydes. Specifically it demonstrates that the yields may be at the lower end of the acceptable range.

Example 4 was repeated except that the starting butyraldehyde was replaced with propionaldehyde. Analysis of the reaction mixture revealed a propionaldehyde (formaldehyde) conversion of 98.6 percent (97.3 percent). The yields of the different products based on propionaldehyde (formaldehyde) were 43.3 percent 2-methyl-2-pentenal, 34.9 percent (61.5 percent) 2,4-dimethyl-glutaraldehyde, 6.5 percent (11.5 percent) alpha-methylacrolein, and 15.3 percent (27.0 percent) heavier materials.

EXAMPLE 7

Propionaldehyde/Formaldehyde Condensation Using Pyrrolidine Catalyst

This example illustrates the use of other cyclic secondary amine catalysts.

Example 5 was repeated replacing the morpholine catalyst with 1.17 volume percent pyrrolidine. The conversion based on propionaldehyde and formaldehyde was 98.6 percent each. The yields of the various products based on propionaldehyde (formaldehyde)

were 37.9 percent 2-methyl-2-pentenal, 14.1 percent (22.7 percent) 2,4-dimethylglutaraldehyde, 5.8 percent (9.3 percent) alpha-methylacrolein, and 42.2 percent (68.0 percent) heavies. In addition, this catalyst was so hot that the contents of the autoclave spontaneously warmed to 60° C. to 70° C. upon mixing before the application of heat. In one instance, the contents of the autoclave spewed out because the temperature had climbed so rapidly. The use of lower catalyst levels moderated this exotherm but led to lower yields of the desired products.

EXAMPLE 8

Propionaldehyde/Formaldehyde Condensation Using 4-Methylpiperidine Catalyst

This example illustrates another secondary amine catalyst.

Example 5 was repeated replacing the morpholine catalyst with 1.16 volume percent 4-methylpiperidine. The conversion of propionaldehyde (formaldehyde) was 98.0 percent (96.4 percent). The yield of the various products based on propionaldehyde (formaldehyde) was 24.0 percent (30.6 percent) 2,4-dimethylglutaraldehyde, 36.2 percent 2-methyl-2-pentenal, 5.0 percent (6.4 percent) alpha-methylacrolein, and 34.8 percent (63.0 percent) heavies.

EXAMPLE 9

Propionaldehyde/Formaldehyde Condensation Using Diethylamine Catalyst

This example illustrates another secondary amine catalyst.

Example 5 was repeated using 1.13 volume percent diethylamine instead of morpholine catalyst. The conversion of propionaldehyde (formaldehyde) was 95.4 percent (99.7 percent). The yields of the various products based on propionaldehyde (formaldehyde) were 26.3 percent (39.7 percent) 2,4-diethylglutaraldehyde, 33.7 percent, 2-methyl-2-pentenal, 3,4 percent (5.1 percent) alpha-methylacrolein, and 36.6 percent (55.2 percent) heavies.

EXAMPLE 10

Propionaldehyde/Formaldehyde Condensation Using Dimethylamine Hydrochloride Salt Catalyst This example illustrates the large increase in the yield of the 2,4-dimethylglutaraldehyde mainly at the expense of 2-methyl-2-pentenal by using the hydrochloride salt catalyst.

Example 5 was repeated using 1.16 w/v percent dimethylamine hydrochloride catalyst instead of morpholine catalyst. The conversion of propionaldehyde (formaldehyde) was 88.5 percent (97.6 percent). The yields of the various products based on propionaldehyde (formaldehyde) were 43.6 percent (57.5 percent) 2,4-dimethylglutaraldehyde, 24.1 percent 2-methyl-2-pentenal, 20.0 percent (26.4 percent) alpha-methylacrolein, and 12.3 percent (16.1 percent) heavies.

EXAMPLE 11

This example shows a chart of the yields from Examples 3–9.

| | | | YIELD | | | | | | | | | |
|---|---|---|---|---|---|---|---|---|---|---|---|---|
| | | | DAG | | DAC | | AA | | FA | | Heav. | |
| Ex. | CA | CF | AlH | FoH | AlH | FoH | AlH | FoH | AlH | FoH | AlH | FoH |
| 3 | 59.5 | 97.1 | 5.1 | 5.2 | 1.5 | — | 28.7 | 29.0 | 50.9 | 51.6 | — | — |
| 4 | 87.6 | 97.8 | 47.9 | 50.8 | 11.7 | — | 22.7 | 24.1 | 2.3 | 2.4 | — | — |
| 5 | 56.1 | 47.6* | 68.7 | 84.2 | 18.9 | — | — | — | — | — | 12.4 | 15.8 |
| 6 | 98.6 | 97.3 | 34.9 | 61.5 | 43.3 | — | 6.5 | 11.5 | — | — | 15.3 | 27.0 |
| 7 | 98.6 | 98.6 | 14.1 | 22.7 | 37.9 | — | 5.8 | 9.3 | — | — | 42.2 | 68.0 |
| 8 | 98.0 | 96.4 | 24.0 | 30.6 | 36.2 | — | 5.0 | — | — | — | 34.8 | 63.0 |
| 9 | 95.4 | 99.7 | 26.3 | 39.7 | 33.7 | — | 3.4 | — | — | — | 36.6 | 55.2 |
| 10 | 88.5 | 97.6 | 43.6 | 57.5 | 24.1 | — | 20.0 | 26.4 | — | — | 12.3 | 16.1 |

*AA Conversion
CA = Conversion of aldehyde
CF = Conversion of formaldehyde
Yield AlH = Yield based on aldehyde converted
Yield FoH = Yield based on formaldehyde converted
DAG = Dialkylglutaraldehyde
DAC = 2,4-Dialkylcrotonaldehyde
AA = 2-Alkylacrolein
FA = 2-formyl-1-alkanal
Heav. = Heavier products The invention has been described in detail with particular reference to preferred embodiments thereof, but it will be understood that variations and modifications can be effected within the spirit and scope of the invention.

What is claimed is:

1. A process for preparing 2,4-disubstituted-1,5-pentanediols comprising the steps of:
   reacting formaldehyde with at least one aldehyde having the formula $RCH_2CHO$, wherein R is hydrogen, or an unsubstituted or substituted aliphatic, aromatic, or aliphatic/aromatic group, at a mole ratio of said aldehyde to said formaldehyde of about 2 to about 7, a temperature of about 40° C. to about 200° C. and in the presence of a catalytic amount of a compound selected from cyclic and acyclic secondary amines or the acid salts thereof to produce a 2,4-disubstituted-glutaraldehyde, and
   hydrogenating said 2,4-disubstituted glutaraldehyde to a 2,4-disubstituted-1,5-pentanediol.

2. A process as claimed in claim 1 further comprising the step of separating said 2,4-disubstituted-glutaraldehyde from the reaction mixture prior to the hydrogenation step.

3. A process as claimed in claim 2 wherein said separation comprises distilling the 2,4-disubstituted glutaraldehyde at low distillation pressures to minimize decomposition of the 2,4-disubstituted glutaraldehyde during said separation.

4. A process as claimed in claim 1 wherein said hydrogenation step comprises hydrogenating said 2,4-disubstituted glutaraldehyde in the presence of a hydrogenation catalyst selected from nickel, palladium, platinium, ruthenium and rhenium.

5. A process as claimed in claim 4 wherein the reaction is conducted at a temperature of about 100° C. to about 140° C. for 1 to 8 hours.

6. A process as claimed in claim 5 wherein said catalyst is present in a concentration of from about 10M to about $10^{-4}$M.

7. A process as claimed in claim 6 wherein the mole ratio of said aldehyde to said formaldehyde is from about 2.5 to about 4.

8. A process as claimed in claim 7 wherein the reaction period comprises 2 to 4 hours at a temperature of about 70° C. to about 90° C. and 2 to 4 hours at a temperature of about 100° C. to about 140° C.

* * * * *